(12) United States Patent
Samuel et al.

(10) Patent No.: US 10,080,717 B2
(45) Date of Patent: *Sep. 25, 2018

(54) COMPOSITION OF HAIR OIL FOR STIMULATION OF HAIR GROWTH, CONTROL OF HAIRFALL, DANDRUFF AND INFECTIONS THEREOF

(71) Applicant: Indfrag Biosciences Inc., Eatontown, NJ (US)

(72) Inventors: Philip Samuel, Bangalore (IN); Boobalarasu Nadar, Bangalore (IN); Roshni Raj, Bangalore (IN)

(73) Assignee: Indfrag Biosciences Inc., Eatontown, NJ (US)

( * ) Notice: Subject to any disclaimer, the term of this patent is extended or adjusted under 35 U.S.C. 154(b) by 243 days.

This patent is subject to a terminal disclaimer.

(21) Appl. No.: 15/272,701

(22) Filed: Sep. 22, 2016

(65) Prior Publication Data

US 2017/0095414 A1    Apr. 6, 2017

Related U.S. Application Data

(63) Continuation of application No. 14/876,470, filed on Oct. 6, 2015, now Pat. No. 9,452,129.

(51) Int. Cl.
| | | |
|---|---|---|
| *A61K 36/00* | (2006.01) | |
| *A61K 8/92* | (2006.01) | |
| *A61K 8/97* | (2017.01) | |
| *A61K 8/37* | (2006.01) | |
| *A61K 8/34* | (2006.01) | |
| *A61Q 7/00* | (2006.01) | |
| *A61Q 5/00* | (2006.01) | |
| *A61K 8/31* | (2006.01) | |
| *A61Q 13/00* | (2006.01) | |
| *A61Q 19/00* | (2006.01) | |

(52) U.S. Cl.
CPC ............... *A61K 8/922* (2013.01); *A61K 8/31* (2013.01); *A61K 8/345* (2013.01); *A61K 8/347* (2013.01); *A61K 8/37* (2013.01); *A61K 8/375* (2013.01); *A61K 8/92* (2013.01); *A61K 8/97* (2013.01); *A61Q 5/006* (2013.01); *A61Q 7/00* (2013.01); *A61Q 13/00* (2013.01); *A61Q 19/007* (2013.01); *A61K 2800/244* (2013.01); *A61K 2800/522* (2013.01)

(58) Field of Classification Search
CPC ...................................................... A61K 36/00
USPC .......................................................... 424/725
See application file for complete search history.

(56) References Cited

U.S. PATENT DOCUMENTS

2009/0074683 A1  3/2009 Nguyen
2014/0242020 A1  8/2014 Meyer et al.

*Primary Examiner* — Michael V Meller
(74) *Attorney, Agent, or Firm* — Gable Gotwals

(57) ABSTRACT

An improved composition of hair oil for stimulation of hair growth, control of hair fall, dandruff and infections thereof. The composition of hair oil comprising active ingredients of Capric Caprylic Tri-Glycerides (CCTG), Mineral oil, Coconut Oil, Ylang Ylang Oil, Di-propylene Glycol, *Centella Asiatica* Extract and Butylated Hydroxy Toulene. The composition of hair oil supports the hair growth and relaxation of the scalp. The composition of hair oil also effectively reduces/remove dandruff and thereby control hair fall in the subject (e.g., not limiting to male/female human). The composition of hair oil additionally demonstrates the properties of cooling effect, darkening of hair and promotion of hair upon continuous use of the hair oil by the subjects. The proposed composition is alternatively used to reduce/remove Psoriasis.

8 Claims, 3 Drawing Sheets

COMPOSITION OF HAIR OIL FOR STIMULATION OF HAIR GROWTH, CONTROL OF HAIRFALL, DANDRUFF AND INFECTIONS THEREOF

CROSS-REFERENCE TO RELATED APPLICATIONS

This application is a continuation application of U.S. patent application Ser. No. 14/876,470 filed Oct. 6, 2015, now U.S. Pat. No. 9,452,129 issued Sep. 27, 2016, which is incorporated herein by reference.

TECHNICAL FIELD

Embodiments are generally related to the field of pharmaceutics, cosmetics and allied industries. Embodiments are also related to composition for stimulation of hair growth, control of hair fall, dandruff and infections thereof. Embodiments are particularly related to an improved composition of oil comprising coconut oil, Ylang Ylang, *Centella Asiatica* Extract and Butylated Hydroxy Toulene and method for preparing the same therefor.

BACKGROUND OF THE INVENTION

Hair loss/hair fall has become an ubiquitous affliction of human beings (both male and female gender) with the growing impact of global pollution and lifestyle changes. Most common reasons for radial or premature hair loss/hair fall are genetic predisposition, endocrine disorders, medication, radiation, chemotherapy, and exposure to chemicals, nutritional factors, generalized or local skin diseases, stress, child birth, Alopecia areata and mechanical damage such as Trichotillomania, hair styling treatment, hair braids and weaves.

In general, the hair in humans is generated by the hair follicles implanted in the scalp. A healthy head of hair is said to contain between 100000 and 150000 hairs, and each hair within this head of hair possesses its own cycle. The life cycle of the hair can be described in three successive physiological phases such as, Anagen, Catagen and Telogen. Anagen is a phase of hair growth which may last from a few weeks to 10 years, Catagen phase is a transient phase of involution of the follicle and ceasing of hair growth with degeneration of the root which may last for a few weeks and Telogen is a phase of shedding of the hair with the root moving up towards the surface by lasting 1 to 5 months. At the end of Telogen phase, the hair therefore disappears from the scalp and this disappearance may extend from a few days to a few months before the follicle is reactivated to give a new hair in the Anagen phase.

Dandruff is a common affliction most usually associated with the human scalp area. It is recognized that skin normally sloughs off the skin surfaces of the human body. In general practice, the skin which is sloughed off is normally washed away at frequent intervals so that the sloughing off process is not noticeable. On the scalp, which is not normally washed as often as other parts of the body, the sloughed-off skin tends to accumulate. This skin together with the natural oils exuded by the scalp form a suitable environment for the growth of bacteria, and in fact certain bacteria are known to be associated with hair fall or hair loss.

Hair loss provokes anxiety and distress which reflects the symbolic and psychosocial importance of hair. Hair loss is a common disorder that affects men and women of all ages and about 50% of men and women suffer from hair loss by the age of 40. Androgenetic alopecia and diffuse hair loss (telogen effluvium) are the common causes, while alopecia areata (patchy balding) affects 1.7% of the population, "Telogen effluvium" develops over a period of several months, is usually, not a permanent form of hair loss, and eventually, the hair follicles can recover. Topical application of biological response modifiers, and antiandrogens are currently available therapies for the management of telogen effluvium (in women, HRT can also be used); however, the low success rate and associated adverse effects limit their clinical use.

Based on the foregoing, it is believed that a need exists for an improved composition of hair oil for stimulation of hair growth, control of hair fall, dandruff and infections thereof, as described in greater detail herein.

SUMMARY OF THE INVENTION

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved hair growth product for stimulation of hair growth, control of hair fall, dandruff and infections thereof.

It is another aspect of the disclosed embodiments to provide for an improved composition of hair oil for stimulation of hair growth, control of hair fall, dandruff and infections thereof.

It is further aspect of the disclosed embodiments to provide for an improved composition comprising coconut oil, Ylang Ylang, *Centella Asiatica* Extract and Butylated Hydroxy Toulene and method for preparing the same thereof.

The aforementioned aspects and other objectives and advantages can now be achieved as described herein. An improved composition of hair oil for stimulation of hair growth, control of hair fall, dandruff and infections thereof. The composition of hair oil comprising active ingredients of Capric Caprylic Tri-Glycerides (CCTG), Mineral oil, Coconut Oil, Ylang Ylang Oil, Di-propylene Glycol, *Centella Asiatica* Extract and Butylated Hydroxy Toulene. The composition of hair oil supports the hair growth and relaxation of the scalp. The composition of hair oil also effectively reduces/removes dandruff and thereby control hair fall in the subject (e.g., not limiting to male/female human). The composition of hair oil additionally demonstrates the properties of cooling effect, darkening of hair and promotion of hair upon continuous use of the hair oil by the subjects. In an alternative embodiment of the present invention, the proposed composition of oil is alternatively used to reduce/remove Psoriasis.

The clinical trial study results prove the efficacy of the proposed composition of hair oil, the composition of hair oil has greater efficacy in controlling the dandruff and thereby promoting improved hair growth in the subjects. The composition of hair oil comprises 50-60% Capric Caprylic Tri-Glycerides (CCTG) which acts as a base for the hair oil, The composition further comprises 10-20% of Mineral oil which is responsible for moisturizing the hair of the subject, 25-35% of Coconut Oil for nourishing the hair and the scalp, 0.5-0.88% of Ylang Ylang Oil for supporting hair growth and relaxation to the scalp, 0.1-0.2% of Di-propylene Glycol which acts as an carrier for fragrance, and 0.01-0.05% of *Centella Asiatica* Extract as an anti-dandruff and anti-hair fall agent and 0.1-0.2% of Butylated Hydroxy Toulene which act as an anti-oxidant.

DEFINITIONS

The following terms shall have the meanings stated therewith:
1. Active ingredient: In the present context the term active ingredient is a composite mixture derived from Capric Caprylic Tri-Glycerides (CCTG), Mineral oil, Coconut Oil, Ylang Ylang Oil, Di-propylene Glycol, *Centella Asiatica* Extract and Butylated Hydroxy Toulene.
2. Composition of Oil: The composition of oil is a mixture of the active ingredients of the proposed invention including Capric Caprylic Tri-Glycerides (CCTG), Mineral oil, Coconut Oil, Ylang Ylang Oil, Di-propylene Glycol, *Centella Asiatica* Extract and Butylated Hydroxy Toulene at a defined ratio which effectively reduces dandruff and thereby control hair fall in the subject
3. Dandruff: Dandruff is a common chronic scalp condition marked by flaking of the skin on the scalp. It is the shedding of dead skin cells from the scalp. As skin cells die, a small amount of flaking is normal. As the epidermal layer continually replaces itself, cells are pushed outward where they eventually die and flake off. Dandruff is produced when the skin of the scalp exfoliates excessively. Another cause of dandruff is fungus, especially an abundance of the fungus *Pitrosporum ovale*.
4. Psoriasis: Psoriasis is a long-term chronic skin problem that causes skin cells to grow too quickly, resulting in thick, white, silvery, or red patches of skin. Normally, skin cells grow gradually and flake off about every 4 weeks. New skin cells grow to replace the outer layers of the skin as they shed. But in psoriasis, new skin cells move rapidly to the surface of the skin in days rather than weeks. They build up and form thick patches called plaques. The patches range in size from small to large. They most often appear on the knees, elbows, scalp, hands, feet, or lower back.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
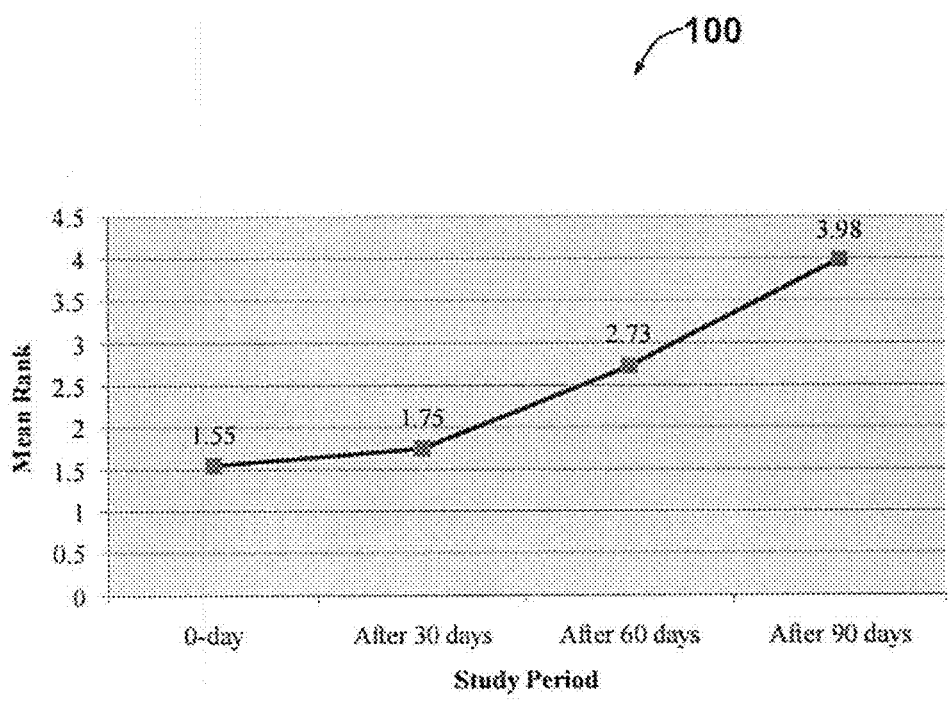
FIG. 1 illustrates a graphical representation of the graph demonstrating the effect of the composition of hair oil on hair population, in accordance with the disclosed embodiments.

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An improved composition of hair oil for stimulation of hair growth, control of hair fall, dandruff and infections thereof. The composition of hair oil comprising active ingredients of Capric Caprylic Tri-Glycerides (CCTG), Mineral oil, Coconut Oil, Ylang Ylang Oil, Di-propylene Glycol, *Centella Asiatica* Extract and Butylated Hydroxy Toulene. The composition of hair oil supports the hair growth and relaxation of the scalp. The composition of hair oil also effectively reduces dandruff and thereby control hair fall in the subject (e.g., not limiting to male/female human).

The composition of hair oil additionally demonstrates the properties of cooling effect, darkening of hair and promotion of hair upon continuous use of the hair oil by the subjects. In an alternative embodiment of the present invention, the proposed composition of oil is alternatively used to reduce/remove Psoriasis. Note that the embodiments disclosed herein are only exemplary embodiments to demonstrate the applications of the proposed invention. The embodiments disclosed herein should not be constituted in any limited sense. The proposed composition of oil can be alternatively adapted in a wide range of other applications other than dandruff and Psoriasis. A person skilled in the art shall appreciate the other applications of the proposed composition of oil within the scope of the invention.

The clinical trial study results prove the efficacy of the proposed composition of hair oil, the composition of hair oil has greater efficacy in controlling the dandruff and thereby promoting improved hair growth in the subjects. The composition of hair oil comprises 50-60% Capric Caprylic Tri-Glycerides (CCTG) which acts as a base for the hair oil, The composition further comprises 10-20% of Mineral oil which is responsible for moisturizing the hair of the subject, 25-35% of Coconut Oil for nourishing the hair and the scalp, 0.5-0.88% of Ylang Ylang Oil for supporting hair growth and relaxation to the scalp, 0.1-0.2% of Di-propylene Glycol which acts as an carrier for fragrance, and 0.01-0.05% of *Centella Asiatica* Extract as an anti-dandruff and anti-hair fall agent and 0.1-0.2% of Butylated Hydroxy Toulene which act as an anti-oxidant. Table-1 illustrates the ratio of the active ingredients used in the composition of oil.

TABLE 1

| S. No | Ingredients | % |
|---|---|---|
| 1 | CCTG | 50-60 |
| 2 | Mineral Oil | 10-20 |
| 3 | Coconut Oil | 25-35 |
| 4 | Ylang Ylang Oil | 0.5-0.8 |
| 5 | Di propylene Glycol | 1-2 |
| 6 | *Centella Asiatica* Extract | 0.01-0.05 |
| 7 | Butylated Hydroxy Toulene | 0.1-0.2 |

FIG. 1 illustrates a graphical representation of the graph 100 demonstrating the effect of the composition of hair oil on hair population, in accordance with the disclosed embodiments. The results 100 reveal that there is good increase in the hair population of the subjects on continuous use of the test oil over the study period. Before study start clinicians have graded the hair population of 90% of the subjects under 'fair' category and remaining 10% between 'poor and fair' category while at the end of the study period clinicians had rated the hair population of the subjects in the grades of 'fair-good-good-good-excellent'. It should be noticed that the clinicians have indicated appreciable changes in the subjects' hair population after 60 days of oil use. There is a steady increase in the mean values from 1.55 before use to 3.98 after 90 days of oil use indicating marked increase in the hair population and the difference in the extent of improvement in the hair population from before use to after 90 days of use results are significant at p<0.001.

Figure 2:
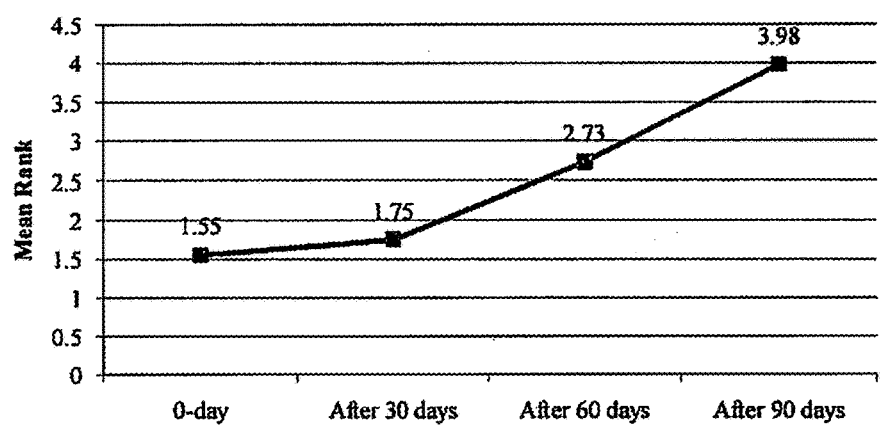
FIG. 2 illustrates a graphical representation of the graph demonstrating the effect of the composition of hair oil on hair length, in accordance with the disclosed embodiments.

FIG. 2 illustrates a graphical representation of the graph 200 demonstrating the effect of the composition of hair oil on hair length, in accordance with the disclosed embodiments. The increase in the length of the hair was evaluated after using the test oil for 90 days. Data projected in the graph 200 demonstrates that the clinicians could perceive good improvement in the increase in the subjects' hair length on using the test oil over the study period.

Clinicians reported 85% of the subjects' hair length under 'fair' cadre before use of the test oil, but at the end of the study period they had reported improvements in all the cases, in 40% of subjects the improvements were between fair-good cadre, in 40% under 'good' cadre and in the remaining 20 percent between 'good and excellent' cadre respectively. The incremental mean scores from 1.55 before use to 3.98 after 90 days of oil use indicates steady increase in the hair length of the subjects, as per clinicians' opinion. The level of significance as represented by the Friedman's Chi-square test, value being 53.691 indicates that it is statistically significant at P<0.001. The increase in hair length can be attributed to the oil effect in inducing the production of a keratinised hair shaft and hair follicles.

Figure 3:
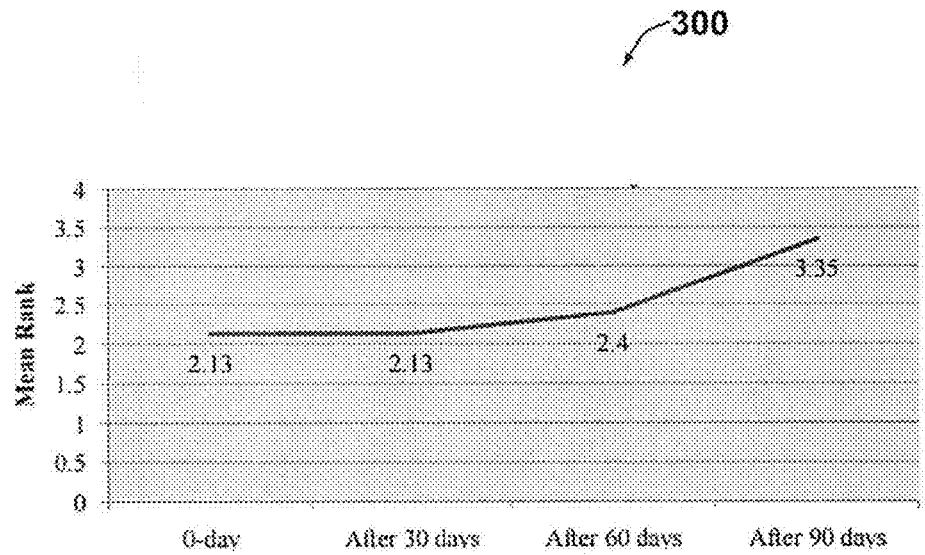
FIG. 3 illustrates a graphical representation of the graph demonstrating the effect of the composition of hair oil on hair density, in accordance with the disclosed embodiments.

FIG. 3 illustrates a graphical representation of the graph 300 demonstrating the effect of the composition of hair oil on hair density, in accordance with the disclosed embodiments. The increase in the density of the subjects hair was evaluated by the clinicians. Data projected in the above table demonstrates that there is increase in the hair density of the subjects' hair after 60 days of oil use. Clinicians rated 20 percent of subject's hair density in the cadre between 'poor and fair' and for 80 percent in the cadre of 'fair' before the study onset. But there was increase in the hair density after the 60th day, on 40% of the participants, they had rated 35% of the subjects hair density improvements between 'fair and good' and remaining 5% under 'good' cadre respectively. There is a steady increase in the mean rank scores from 2.13 before use to 3.35 in the end of 90 day study period. The effectiveness of the test oil in increasing the hair density is further substantiated by the Friedman's Chi-square value of 30.797 which is statistically significant at p<0.001.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

We claim:

1. A method for stimulation of hair growth, control of hair fall, dandruff and infections consisting essentially of administering a composition consisting essentially of therapeutically effective amounts of:
   Capric Caprylic Tri-Glycerides;
   mineral oil;
   coconut oil;
   Ylang Ylang oil;
   Di-propylene Glycol;
   *Centella Asiatica* Extract; and
   Butylated Hydroxy Toluene to a human in need thereof.

2. The method of claim 1, wherein 50-60% of the composition is Capric Caprylic Tri-Glycerides.

3. The method of claim 1, wherein 10-20% of the composition is mineral oil.

4. The method of claim 1, wherein 25-35% of the composition is coconut oil.

5. The method of claim 1, wherein 0.5-0.88% of the composition is Ylang Ylang oil.

6. The method of claim 1, wherein 0.1-0.2% of the composition is Di-propylene Glycol.

7. The method of claim 1, wherein 0.01-0.05% of the composition is *Centella Asiatica* Extract.

8. The method of claim 1, wherein 0.1-0.2% of the composition is Butylate Hydroxy Toluene.

* * * * *